(12) United States Patent
Wichert et al.

(10) Patent No.: US 7,820,863 B2
(45) Date of Patent: Oct. 26, 2010

(54) PROCESS FOR PURIFYING MESOTRIONE

(75) Inventors: Julie Marie Wichert, Bucks, AL (US); Alan Henry Benke, Bucks, AL (US); Regine Laure Guidetti-Grep, Monthey (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 369 days.

(21) Appl. No.: 10/573,723

(22) PCT Filed: Oct. 1, 2004

(86) PCT No.: PCT/EP2004/010960
§ 371 (c)(1),
(2), (4) Date: Feb. 21, 2007

(87) PCT Pub. No.: WO2005/035487
PCT Pub. Date: Apr. 21, 2005

(65) Prior Publication Data
US 2008/0045751 A1  Feb. 21, 2008

(30) Foreign Application Priority Data
Oct. 2, 2003 (GB) .................. 0323090.1
Jul. 1, 2004 (GB) .................. 0414816.9

(51) Int. Cl.
*C07C 315/00* (2006.01)

(52) U.S. Cl. ...................................... 568/30

(58) Field of Classification Search ............... 568/30, 568/310, 341, 346, 384, 388, 314; 504/348; 562/429
See application file for complete search history.

(56) References Cited

U.S. PATENT DOCUMENTS

| 4,695,673 | A  | * | 9/1987  | Heather et al. ............. 568/310 |
| 4,937,386 | A  | * | 6/1990  | Ueda et al. ................. 504/348 |
| 5,591,890 | A  | * | 1/1997  | Jacobson .................... 562/412 |
| 6,218,579 | B1 | * | 4/2001  | Jones et al. ................. 568/309 |
| 6,809,206 | B2 | * | 10/2004 | Wojtkowski .............. 548/364.4 |
| 7,285,678 | B2 | * | 10/2007 | Javdani et al. ............. 562/429 |

FOREIGN PATENT DOCUMENTS

WO   WO-02-076934 A   10/2002

OTHER PUBLICATIONS

Jacobson et al., New air oxidation route to ortho-nitroaromatic acids, Chemical Industries (Dekker) (1996), 68(Catalysis of Organic Reactions), 87-96.*

* cited by examiner

*Primary Examiner*—Daniel M Sullivan
*Assistant Examiner*—Chukwuma O Nwaonicha
(74) *Attorney, Agent, or Firm*—William A. Teoli, Jr.

(57) ABSTRACT

A process for reducing the levels of undesirable impurities in a mesotrione sample is disclosed, said process comprising the steps of:
(i) forming a mesotrione enolate solution in an aqueous solvent,
(ii) carrying out one or more purification processes, and
(iii) crystallizing the purified mesotrione out of solution.

5 Claims, No Drawings

PROCESS FOR PURIFYING MESOTRIONE

This application is a 371 of International Application No. PCT/EP2004/010960 filed Oct. 1, 2004, which claims priority to GB0323090.1 filed Oct. 2, 2003, and GB0414816.9 filed Jul. 1, 2004, the contents of which are incorporated herein by reference.

The present invention relates to a novel process for reducing the level of impurities in a mesotrione sample.

Mesotrione (2-(2'-nitro-4'-methylsulphonyl benzoyl)-1,3-cyclohexanedione) is a selective corn herbicide and has the structure of formula (I)

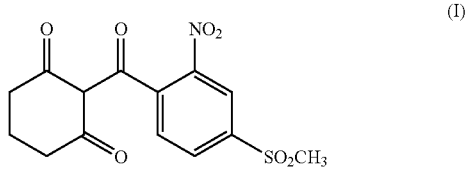

Mesotrione is prepared by reacting 2-nitro-4-methylsulphonyl benzoyl chloride with cyclohexanedione to give the enol ester, followed by a rearrangement reaction to give mesotrione, as shown in the following reaction scheme:

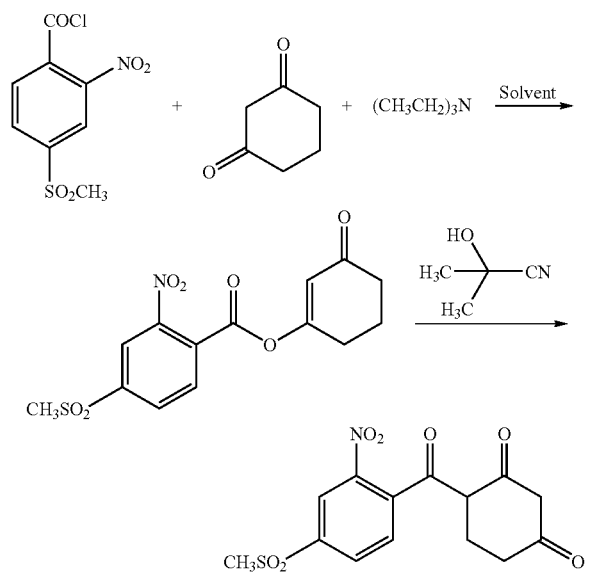

2-Nitro-4-methylsulphonyl benzoyl chloride (NMSBC) is prepared from the corresponding 2-nitro-4-methylsulphonyl benzoic acid (NMSBA), which in turn is prepared by oxidation of 2-nitro-4-methylsulphonyl toluene (NMST). More details on the preparative route may be found in U.S. Pat. No. 4,695,673.

However, we have found that this process generally results in undesirable level of impurities being present in the final mesotrione product. One method we have found of reducing the impurities is to subject the NMSBA to a purification process before converting to NMSBC, as described in more detail in WO02/076934. However, purifying the NMSBA does not always guarantee that the final product is free from, or has sufficiently low levels of, these impurities.

It is therefore an object of the present invention to provide an improved process for reducing the level of impurities in a mesotrione sample.

Accordingly, the present invention provides a process for reducing the levels of impurities in a mesotrione sample, said process comprising the steps of:
 (i) forming a mesotrione enolate solution in an aqueous solvent,
 (ii) carrying out one or more purification processes, and
 (iii) crystallising the purified mesotrione out of solution.

Optionally, the process may further comprise a distillation step, which is suitably carried out prior to forming the mesotrione enolate. Generally, the distillation step will only, although not necessarily, be used if the mesotrione product has not been isolated after its preparation.

The enolate solution may be formed by the addition of an appropriate base, for example NaOH, KOH, NH$_4$OH, pyridine or triethylamine; suitably the enolate is formed by the addition of NaOH or KOH. Suitably, the aqueous solvent is water, although in some cases an additional solvent, for example acetonitrile, methanol, ethanol, acetone, dimethylformamide etc, may be required to ensure complete dissolution of the mesotrione enolate. The mesotrione enolate solution is suitably formed at a pH of 6-13.

The one or more purification processes may be selected from the following:
 (a) filtration,
 (b) adsorption with suitable sorbent, such as carbon, clay etc.,
 (c) extraction with an organic solvent, or
 (d) decantation.

Any number of the purification processes may be carried out and they may be performed in any order. Suitably, at least two purification processes are carried out and preferably at least three. The purification processes will now be described in further detail.

Filtration is carried out to remove any insoluble impurities that remain in the mesotrione enolate solution. The filtration may be carried out by any suitable method known in the art to a skilled person.

Adsorption treatment adsorbs impurities from the mesotrione enolate solution. A mesotrione enolate solution of suitably 1-30%, and preferably 8-11% is contacted with carbon in a batch or continuous fashion for a period of several hours. Concentration of the adsorbent solution relative to the concentration of mesotrione in the enolate is suitably 2-40% and preferably 10-20%. The pH for adsorption treatment is suitably between pH 5 and 13, and preferably between pH 9 and 11.

Extraction with an organic solvent is carried out to remove any impurities, which are soluble in the organic phase but insoluble in the aqueous phase. An organic solvent is added to the mesotrione enolate aqueous solution and some impurities will preferentially dissolve in the organic phase which is then removed and discarded. The mesotrione enolate aqueous solution may be 'washed' a number of times with organic solvent, such as once, twice, three times, four times etc or continuously contacted in a counter current column. It is unlikely that more than four 'washings' would be required as all the impurities soluble in the organic solvent are likely to have been removed after this number of 'washings'. Suitable organic solvents will be known to those skilled in the art, but may include benzonitrile, acetonitrile/xylene, xylene, methylene chloride, MIBK, ethyl ether, n-hexane and 1,2-dichloroethane.

Decantation simply refers to the removal of any organic solvent from the solution. Organic solvent is likely to remain with the mesotrione enolate aqueous solution if the mesotrione product has not been isolated after its preparation and no distillation step is carried out. Removal of the organic solvent will remove any impurities soluble in the organic solvent, but insoluble in the aqueous solution.

The optional distillation step is suitably carried out prior to forming the mesotrione enolate solution and will remove any organic solvent remaining after the condensation/rearrangement reaction described above.

The crystallisation step may be carried out by any method known to those skilled in the art. For example, the process may be a batch method, a semi-batch method or a continuous crystallisation method. The crystallisation is suitably effected by reducing the pH of the mesotrione enolate solution, for example by the controlled addition of acid such as hydrochloric acid. Seed crystals of mesotrione may be used to assist the crystallisation process. Optionally, a water-soluble solvent may be added, since the presence of a water soluble solvent such as acetonitrile aids in reducing the amount of impurities present at this point.

In one specific embodiment of the invention, the process comprises: a distillation step; formation of a mesotrione enolate solution, preferably the potassium enolate; one or more purification steps; and crystallisation of mesotrione.

In a second specific embodiment of the invention, the process comprises: formation of a mesotrione enolate solution, preferably the potassium enolate; decantation, filtration and adsorption treatment, carried out in any order (although preferably the decantation process is carried out first); and crystallisation of mesotrione.

By carrying out the process according to the invention, the level of impurities in the final mesotrione product is reduced to an acceptable level.

A further advantage of the process of the present invention is that is can be integrated into the mesotrione manufacturing process, thus eliminating the need for isolation of crude mesotrione followed by purification. Accordingly, a further aspect of the invention provides an integrated manufacturing/purification process for mesotrione, said process comprising the steps of:

(i) reacting cyclohexanedione with 2-nitro-4-methylsulphonyl benzoyl chloride (NMSBC) to form an enol ester followed by a rearrangement process to give mesotrione;

(ii) formation of mesotrione enolate in aqueous solution;

(iii) carrying out one or more purification processes, and (iv) crystallising the purified mesotrione out of solution.

Optionally, the process may further comprise a distillation step, which is suitably carried out prior to forming the mesotrione enolate.

Optionally, the NMSBC is first subjected to a carbon purification treatment.

Thus, one specific embodiment of this aspect of the invention provides an integrated manufacturing/purification process for mesotrione, said process comprising: reacting cyclohexanedione with 2-nitro-4-methylsulphonyl benzoyl chloride (NMSBC) to form an enol ester followed by a rearrangement process to give mesotrione; a distillation step; formation of potassium enolate mesotrione solution; one or more purification steps; and crystallisation of mesotrione.

A second specific embodiment of this aspect of the invention provides an integrated manufacturing/purification process for mesotrione, said process comprising reacting cyclohexanedione with 2-nitro-4-methylsulphonyl benzoyl chloride (NMSBC) to form an enol ester followed by a rearrangement process to give mesotrione; formation of a mesotrione enolate solution, preferably the potassium enolate; decantation, filtration and adsorption treatment, carried out in any order (although preferably the decantation process is carried out first); and crystallisation of mesotrione.

Previously, in order to attempt to obtain a final mesotrione product with an acceptable level of impurities, it was necessary to subject the crude NMSBA (prepared by oxidation of NMST) to a purification process, as described in WO02/076934. However, as mentioned above, this did not always give sufficiently low levels of impurities in the final mesotrione product to be acceptable. Surprisingly, we have now found that if the process of the invention is followed, the purification of NMSBA is not essential or at most only 'partial' purification, such as one step as opposed to the two or three disclosed in WO02/076934, is required; that is acceptable levels of impurities can be obtained in the final mesotrione product when less purified or even crude NMSBA is used. Accordingly, a yet further aspect of the invention provides a process for preparing mesotrione, said method comprising:

(i) Oxidation of NMST to give crude NMSBA;

(ii) conversion of NMSBA to NMSBC;

(iii) reacting cyclohexanedione with 2-nitro-4-methylsulphonyl benzoyl chloride (NMSBC) to form an enol ester followed by a rearrangement process to give mesotrione;

(iv) formation of mesotrione enolate in aqueous solution;

(v) carrying out one or more purification processes, and (vi) crystallising the purified mesotrione out of solution.

Optionally, the process may further comprise partial purification of crude NMSBA.

Optionally, the process may further comprise a distillation step, which is suitably carried out prior to forming the mesotrione enolate.

Thus one specific embodiment of this aspect of the invention provides a process for preparing mesotrione, said process comprising: oxidation of NMST to give crude NMSBA; optional partial purification of crude NMSBA; conversion of NMSBA to NMSBC; reacting cyclohexanedione with 2-nitro-4-methylsulphonyl benzoyl chloride (NMSBC) to form an enol ester followed by a rearrangement process to give mesotrione; a distillation step; formation of mesotrione enolate solution, preferably the potassium enolate; one or more purification steps; and crystallisation of mesotrione.

A second embodiment of this aspect of the invention provides a process for preparing mesotrione, said process comprising: oxidation of NMST to give crude NMSBA; optional partial purification of crude NMSBA; conversion of NMSBA to NMSBC; reacting cyclohexanedione with 2-nitro-4-methylsulphonyl benzoyl chloride (NMSBC) to form an enol ester followed by a rearrangement process to give mesotrione; formation of a mesotrione enolate solution; decantation, filtration and adsorption treatment carried out in any order; and crystallisation of mesotrione.

The present invention will now be described further by way of example only.

EXAMPLE 1

This is an example of the solid adsorption treatment (using carbon as adsorbent) of previously isolated mesotrione which had high levels of impurities. The additional purification option of pre-filtration was used in these examples.

TABLE 1

| Example No. | Treatment | Original Impurities Content (PPM) | Impurities Content after Treatment (PPM) | % Reduction in Impurities Content |
|---|---|---|---|---|
| 1A | Already isolated mesotrione was dissolved into a 10% enolate solution at pH 9.5 with KOH. The mixture was pre-filtered and contacted with 15% carbon for 2.5 hours before being filtered and batch crystallized following standard lab procedures. | 7900 | 2800 | 65% |
| 1B | Already isolated mesotrione was dissolved into a 10% enolate solution at pH 9.5 with KOH. The mixture was pre-filtered and contacted with 15% carbon for 2.5 hours before being filtered and batch crystallized following standard lab procedures. | 7400 | 4500 | 39% |
| 1C | Already isolated mesotrione was dissolved into a 10% enolate solution at pH 9.5 with NaOH/acetonitrile. The enolate was pre-filtered and contacted with 15% carbon for 2.5 hours before being filtered and batch crystallized following standard lab procedures. | 7400 | 2300 | 69% |
| 1D | Already isolated mesotrione was dissolved into a 10% enolate solution at pH 9.5 with NaOH/acetonitrile. The enolate was pre-filtered and batch carbon treated with 9% carbon for 3 hours. The carbon was filtered and the enolate was crystallized in a continuous reactor following standard lab procedures. | 8800 | 1900 | 78% |
| 1E | Already isolated mesotrione was dissolved into a 10% enolate solution at pH 9.5 with triethylamine. The enolate was pre-filtered and batch carbon treated with 9% carbon for 3 hours. The carbon was filtered and the enolate was crystallized in a continuous reactor following standard lab procedures. | 8800 | 3100 | 65% |
| 1F | Already isolated mesotrione was dissolved into a 10% enolate solution at pH 9.5 with NaOH/acetonitrile. The mixture was pre-filtered and contacted with 15% carbon for 2.5 hours before being filtered and batch crystallized following standard lab procedures. | 7900 | 4600 | 42% |
| 1G | Already isolated mesotrione was dissolved into a 10% enolate solution at pH 9.5 with NaOH. The mixture was pre-filtered and contacted with 15% carbon for 2.5 hours before being filtered and batch crystallized following standard lab procedures. | 7400 | 4600 | 38% |

EXAMPLE 2

This is an example of a solvent extraction treatment of previously isolated mesotrione which had high levels of impurities.

TABLE 2

| Example No. | Treatment | Original Impurities Content (PPM) | Impurities Content after Treatment (PPM) | % Reduction in Impurities Content |
|---|---|---|---|---|
| 2A | Already isolated mesotrione was dissolved into a 10% enolate solution at pH 12.5 with KOH. The mixture was contacted with 1,2-dichloroethane, the 1,2-dichloroethane was extracted, and the remaining aqueous layer was batch | 8000 | 4100 | 49% |

TABLE 2-continued

| Example No. | Treatment | Original Impurities Content (PPM) | Impurities Content after Treatment (PPM) | % Reduction in Impurities Content |
|---|---|---|---|---|
| 2B | crystallized following standard lab procedures.<br>Already isolated mesotrione was dissolved into a 10% enolate solution at pH 12.5 with KOH. The mixture was contacted with benzonitrile, the benzonitrile was extracted, and the remaining aqueous layer was batch crystallized following standard lab procedures. | 8000 | 4300 | 46% |

EXAMPLE 3

This is an example of an integrated adsorption treatment of in-process mesotrione enolate. NMSBA purified by standard procedures was used as the starting material. The mixture was distilled before the enolate treatments and the purification element of pre-filtration was included. Different adsorbent loadings are shown in the examples in this table.

TABLE 3

| Example No. | Treatment | Original Impurities Content (PPM) | Impurities Content after Treatment (PPM) | % Reduction in Impurities Content |
|---|---|---|---|---|
| 3A | Mesotrione was made using the standard process from NMSBA purified by standard procedures. After the distillation, an enolate solution at pH 9.5 was formed with KOH. The mixture was pre-filtered and contacted with 13% carbon for 2 hours before being filtered and batch crystallized following standard lab procedures. | 13800 | 11100 | 20% |
| 3B | Mesotrione was made using the standard process from NMSBA purified by standard procedures. After the distillation, an enolate solution at pH 9.5 was formed with KOH. The mixture was pre-filtered and contacted with 27% carbon for 3.5 hours before being filtered and batch crystallized following standard lab procedures. | 13800 | 5100 | 63% |
| 3C | Mesotrione was made using the standard process from NMSBA purified by standard procedures. After the distillation, an enolate solution at pH 9.5 was formed with KOH. The mixture was pre-filtered and contacted with 40% carbon for 2 hours before being filtered and batch crystallized following standard lab procedures. | 13800 | 5700 | 59% |
| 3D | Mesotrione was made using the standard process from NMSBA purified by standard procedures. After the distillation, an enolate solution at pH 9.5 was formed with KOH. The mixture was pre-filtered and contacted with 53% carbon for 2 hours before being filtered and batch crystallized following standard lab procedures. | 13800 | 5800 | 58% |
| 3E | Mesotrione was made using the standard process from NMSBA purified by standard procedures. After the distillation, an enolate solution at pH 9.5 was formed with KOH. The mixture was pre-filtered and contacted with 5% carbon for 2 hours before being filtered and batch crystallized following standard lab procedures. | 17900 | 15900 | 11% |
| 3F | Mesotrione was made using the standard process from NMSBA purified by standard procedures. After the distillation, an enolate solution at pH 9.5 was formed with KOH. The mixture was pre-filtered and contacted with 10% carbon for 2 hours | 17900 | 15000 | 16% |

TABLE 3-continued

| Example No. | Treatment | Original Impurities Content (PPM) | Impurities Content after Treatment (PPM) | % Reduction in Impurities Content |
|---|---|---|---|---|
| | before being filtered and batch crystallized following standard lab procedures. | | | |
| 3G | Mesotrione was made using the standard process from NMSBA purified by standard procedures. After the distillation, an enolate solution at pH 9.5 was formed with KOH. The mixture was pre-filtered and contacted with 20% carbon for 2 hours before being filtered and batch crystallized following standard lab procedures. | 17900 | 12300 | 31% |

EXAMPLE 4

This is an example of an integrated adsorption treatment of in process mesotrione enolate. NMSBA purified by standard procedures was used as the starting material. The mixture was distilled before the enolate treatment, and the purification element of pre-filtration was included. Different filtration conditions are used in the examples in this table.

TABLE 4

| Example No. | Treatment | Original Impurities Content (PPM) | Impurities Content after Treatment (PPM) | % Reduction in Impurities Content |
|---|---|---|---|---|
| 4A | Mesotrione was made using the standard process from NMSBA purified by standard procedures. After the distillation, an enolate solution at pH 7 was formed with KOH. The mixture was pre-filtered and contacted with 10% carbon for 2 hours before being filtered and batch crystallized following standard lab procedures. | 15800 | 7400 | 53% |
| 4B | Mesotrione was made using the standard process from NMSBA purified by standard procedures. After the distillation, an enolate solution at pH 7 was formed with KOH. The mixture was pre-filtered and contacted with 10% carbon for 2 hours before being filtered and batch crystallized following standard lab procedures. | 15800 | 7700 | 51% |
| 4C | Mesotrione was made using the standard process from NMSBA purified by standard procedures. After the distillation, an enolate solution at pH 9.5 was formed with KOH. The mixture was pre-filtered and contacted with 10% carbon for 2 hours before being filtered and batch crystallized following standard lab procedures. | 15800 | 10400 | 34% |
| 4D | Mesotrione was made using the standard process from NMSBA purified by standard procedures. After the distillation, an enolate solution at pH 9.5 was formed with KOH. The mixture was pre-filtered and contacted with 10% carbon for 2 hours before being filtered and batch crystallized following standard lab procedures. | 15800 | 8600 | 46% |

EXAMPLE 5

This is an example of an integrated solvent extraction treatment of in process mesotrione enolate. Crude NMSBA was used as the starting material. The mixture was distilled before the enolate treatment.

TABLE 5

| Example No. | Treatment | Original Impurities Content (PPM) | Impurities Content after Treatment (PPM) | % Reduction in Impurities Content |
|---|---|---|---|---|
| 5A | Mesotrione was made using the standard process from crude NMSBA. After the distillation, an enolate solution at pH 13 was formed with KOH. The mixture was contacted with 1,2-dichloroethane, the 1,2-dichloroethane was extracted, and the remaining aqueous layer was batch crystallized following standard lab procedures. | 11000 | 7800 | 29% |

EXAMPLE 6

This is an example of an integrated adsorption treatment of in process mesotrione enolate. Partially purified NMSBA was used as the starting material. The mixture was distilled before the enolate treatment.

TABLE 6

| Example No. | Treatment | Original Impurities Content (PPM) | Impurities Content after Treatment (PPM) | % Reduction in Impurities Content |
|---|---|---|---|---|
| 6A | Mesotrione was made using the standard process from partially purified NMSBA. After the distillation, an enolate solution at pH 5 was formed with NaOH and ACN. The mixture was contacted with 20% carbon for 2 hours before being filtered and batch crystallized following standard lab procedures. | 13300 | 6300 | 53% |
| 6B | Mesotrione was made using the standard process from partially purified NMSBA(. After the distillation, an enolate solution at pH 9 was formed with NaOH and ACN. The mixture was contacted with 20% carbon for 2 hours before being filtered and batch crystallized following standard lab procedures. | 8500 | 4900 | 42% |

EXAMPLE 7

This is an example of an integrated column adsorption treatment of in process mesotrione enolate. Crude NMSBA was used as the starting material. The mixture was distilled before the enolate treatment.

TABLE 7

| Example No. | Treatment | Original Impurities Content (PPM) | Impurities Content after Treatment (PPM) | % Reduction in Impurities Content |
|---|---|---|---|---|
| 7A | Mesotrione was made from crude NMSBA following standard lab procedures. After the distillation, an enolate solution at pH 9.5 was formed with KOH. The mixture was pre-filtered and sent through a carbon column such that there was 14.9% carbon usage. Samples were batch crystallized following standard lab procedures. | 11400 | 10500 | 8% |
| 7B | Mesotrione was made from crude NMSBA following standard lab procedures. After the distillation, an enolate solution at pH 9.5 was formed with KOH. The mixture was pre-filtered and sent through a carbon column such that there was 5.08% carbon usage. Samples were batch crystallized following standard lab procedures. | 11400 | 10100 | 11% |
| 7C | Mesotrione was made from crude NMSBA following standard lab procedures. After the distillation, an enolate solution at pH 9.5 was formed with KOH. The mixture was pre-filtered and sent through a carbon column such that there was 2.93% carbon usage. Samples were batch crystallized following standard lab procedures. | 11400 | 6600 | 42% |

EXAMPLE 8

This is an example of an integrated adsorption treatment of in process mesotrione enolate. Purified or crude NMSBA was used as the starting material. TEA decantation is included as a purification element. The mixture was distilled before the enolate treatment.

TABLE 8

| Example No. | Treatment | Original Impurities Content (PPM) | Impurities Content after Treatment (PPM) | % Reduction in Impurities Content |
|---|---|---|---|---|
| 8A | Mesotrione was made from crude NMSBA by the standard process. An enolate solution at pH 13 was formed with KOH. The TEA was decanted, and the enolate was contacted with 20% carbon for 2 hours at pH 9.5 before being filtered and batch crystallized following standard lab procedures. | 11400 | 5600 | 51% |
| 8B | Mesotrione was made from crude NMSBA by the standard process. After the distillation, an enolate solution at pH 13 was formed with KOH. The TEA was decanted, and the enolate was contacted with 20% carbon for 2 hours at pH 9.5 before being filtered and batch crystallized following standard lab procedures. | 20600 | 8900 | 57% |
| 8C | Mesotrione was made from crude NMSBA by the standard process. After the distillation, an enolate solution at pH 13 was formed with KOH. The TEA was decanted, and the enolate was contacted with 20% carbon for 2 hours at pH 9.5 before being filtered and batch crystallized following standard lab procedures. | 15000 | 6300 | 58% |
| 8D | Mesotrione was made from purified NMSBA by the standard process. An enolate solution at pH 13 was formed with | 6300 | 3400 | 46% |

TABLE 8-continued

| Example No. | Treatment | Original Impurities Content (PPM) | Impurities Content after Treatment (PPM) | % Reduction in Impurities Content |
|---|---|---|---|---|
| | KOH. The TEA was decanted, and the enolate was contacted with 20% carbon for 2 hours at pH 9.5 before being filtered and batch crystallized following standard lab procedures. | | | |
| 8E | Mesotrione was made from purified NMSBA by the standard process. An enolate solution at pH 13 was formed with KOH after the completion of the solvent distillation. The TEA was decanted, and the enolate was contacted with 20% carbon for 2 hours at pH 9.5 before being filtered and batch crystallized following standard lab procedures. | 7300 | 2900 | 60% |
| 8F | Mesotrione was made from purified NMSBA by the standard process. An enolate solution at pH 13 was formed with KOH after the completion of the solvent distillation. The TEA was decanted, and the enolate was contacted with 20% carbon for 2 hours at pH 9.5 before being filtered and batch crystallized following standard lab procedures. | 6600 | 3300 | 50% |

EXAMPLE 9

This is an example of the effect of the presence of acetonitrile during crystallization on the impurity content of mesotrione. An integrated purification was done which used the purification elements of TEA decant and the presence of acetonitrile during the crystallization. The mixture was distilled before the enolate treatment. Crude NMSBA was used as the starting material.

TABLE 9

| Example No. | Treatment | Original Impurities Content (PPM) | Impurities Content after Treatment (PPM) | % Reduction in Impurities Content |
|---|---|---|---|---|
| 9A | Mesotrione was made from crude NMSBA using the standard process. After solvent distillation, a potassium enolate solution at pH 13 was made and the TEA was decanted. The enolate was batch crystallized following standard lab procedures except that acetonitrile was present during the crystallization. | 21800 | 12800 | 41% |
| 9B | Mesotrione was made from crude NMSBA using the standard process. After solvent distillation, a potassium enolate solution at pH 13 was made and the TEA was decanted. The enolate was batch crystallized following standard lab procedures except that acetonitrile was present during the crystallization. | 21800 | 12800 | 41% |
| 9C | Mesotrione was made from crude NMSBA using the standard process. After solvent distillation, a potassium enolate solution at pH 13 was made and the TEA was decanted. The enolate was batch crystallized following standard lab procedures except that acetonitrile was present during the crystallization. | 30900 | 9000 | 71% |

EXAMPLE 10

This is an example of the integrated process starting with crude NMSBA in which a partial NMSBA purification is incorporated directly into the process. The purification elements of decantation and adsorption treatment are used in these examples.

TABLE 10

| Example No. | Treatment | Original Impurities Content (PPM) | Impurities Content after Treatment (PPM) | % Reduction in Impurities Content |
|---|---|---|---|---|
| 10A | Mesotrione was made from the integrated process starting with crude NMSBA in water which was partially purified and distilled to remove water. Benzonitrile was added to make a NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | 2900 | 2500 | 53% |
| 10B | Mesotrione was made from the integrated process starting with crude NMSBA in water which was partially purified and distilled to remove water. Benzonitrile was added to make a NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | 2900 | 1100 | 62% |
| 10C | Mesotrione was made from the integrated process starting with crude NMSBA in water which was partially purified and distilled to remove water. Benzonitrile was added to make a NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | 2900 | 2100 | 28% |
| 10D | Mesotrione was made from the integrated process starting with crude NMSBA in water which was partially purified and distilled to remove water. Benzonitrile was added to make a NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at | 2900 | 1600 | 45% |

TABLE 10-continued

| Example No. | Treatment | Original Impurities Content (PPM) | Impurities Content after Treatment (PPM) | % Reduction in Impurities Content |
|---|---|---|---|---|
| | pH 9.5 before being filtered and batch crystallized following standard lab procedures. | | | |
| 10E | Mesotrione was made from the integrated process starting with crude NMSBA in water which was partially purified and distilled to remove water. Benzonitrile was added to make a NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | 2900 | 1900 | 34% |
| 10F | Mesotrione was made from the integrated process starting with crude NMSBA in water which was partially purified and distilled to remove water at pH 0.8. Benzonitrile was added to make a 20% NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 13 before being filtered and batch crystallized following standard lab procedures. | 2900 | 1500 | 48% |
| 10G | Mesotrione was made from the integrated process starting with crude NMSBA in water which was partially purified and distilled to remove water. Benzonitrile was added to make a NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | 4900 | 3100 | 37% |
| 10H | Mesotrione was made from the integrated process starting with crude NMSBA in water which was partially purified and distilled to remove water. Benzonitrile was added to make NMSBA solution and the remaining water was distilled. Inorganic salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | 3200 | 2500 | 22% |
| 10I | Mesotrione was made from the integrated process starting with crude NMSBA in water which was partially purified and distilled to remove water. Benzonitrile was added to make a NMSBA solution and the remaining water was distilled. Inorganic | 3200 | 2000 | 38% |

TABLE 10-continued

| Example No. | Treatment | Original Impurities Content (PPM) | Impurities Content after Treatment (PPM) | % Reduction in Impurities Content |
|---|---|---|---|---|
| | salts were filtered from the acid chloride after excess phosgene removal. The C/R proceeded by normal reaction conditions. An enolate solution at pH 13 was formed with KOH. The TEA and benzonitrile were decanted and the enolate was contacted with 20% carbon for 2 hours at pH 9.5 before being filtered and batch crystallized following standard lab procedures. | | | |

EXAMPLE 11

Previously isolated mesotrione, made from crude NMSBA, was dissolved by addition of dilute potassium hydroxide to form a 9.1% w/w solution of potassium enolate at pHs 7, 9.5 and 11, respectively. The very small amount of residual solid was removed by filtration.

Extraction

The aqueous solution of potassium enolate of mesotrione (183 g) was extracted with solvent (150 ml) four times. The phases were separated after each extraction and the solvent phase was discarded. After the fourth extraction, the mesotrione was recovered from the aqueous phase by continuous crystallisation according to standard procedure. Analysis showed reduction of the impurities (Table 11A). The figures in parenthesis are the percentage of the impurities remaining after treatment.

TABLE 11A

| | Sum of impurities in mesotrione sample (%) | | | |
|---|---|---|---|---|
| Solvent | Before | After pH 7 | After pH 9.5 | After pH 11 |
| MIBK | 3.419 | 0.258 (7.55%) | 1.305 (38.2%) | 1.308 (38.3%) |
| Ethyl acetate | 3.419 | 1.997 (58.4%) | 1.941 (56.8%) | 2.098 (61.4%) |
| Benzonitrile | 3.419 | 1.991 (58.2%) | 1.018 (29.8%) | 1.652 (48.3%) |
| 2-ethylhexanol | 5.627 | 0.182 (3.2%) | 1.361 (24.2%) | 1.217 (21.6%) |

Adsorption

The aqueous solution of potassium enolate of mesotrione (183 g) was stirred with 5 g adsorbent at ambient temperature (~25° C.) for 30 minutes. The adsorbent was removed by filtration and the mesotrione was recovered from the aqueous phase by continuous crystallisation according to standard procedure. Analysis showed reduction of the impurities (Table 11B). The figures in parenthesis are the percentage of the impurities remaining after treatment.

TABLE 11B

| | Sum of impurities in mesotrione sample (%) | | | |
|---|---|---|---|---|
| Adsorbent | Before | After pH 7 | After pH 9.5 | After pH 11 |
| Ambersorb 348F | 5.627 | 0.383 (6.81%) | 0.680 (12.1%) | 0.171 (3.04%) |
| Amberlite XAD4 | 5.627 | 0.892 (15.9%) | 1.692 (30.1%) | |
| Amberlite XAD16 | 3.419 | 0.245 (7.17%) | 0.063 (1.84%) | 0.145 (4.24%) |
| Molecular sieves 5A | 5.627 | 1.414 (25.1%) | | 1.792 (31.8%) |

What is claimed is:

1. A process for preparing mesotrione, said process comprising:
    (i) Oxidation of 2-nitro-4-methylsulphonyl toluene (NMST) to give crude 2-nitro-4-methylsulphonyl benzoic acid (NMSBA);
    (ii) conversion of NMSBA to 2-nitro-4-methylsulphonyl benzoyl chloride- (NMSBC);
    (iii) reacting cyclohexanedione with 2-nitro-4-methylsulphonyl benzoyl chloride (NMSBC) to form an enol ester followed by a rearrangement process to give mesotrione;
    (iv) formation of mesotrione enolate in aqueous solution;
    (v) carrying out one or more purification processes on the mesotrione enolate formed in iv, and
    (vi) crystallizing the purified mesotrione enolate out of solution.

2. The process of claim 1, wherein the process further comprises partial purification of the crude NMSBA.

3. The process of claim 1, wherein the process further comprises a distillation step.

4. A process for preparing mesotrione, said process comprising: oxidation of NMST to give crude NMSBA; optional partial purification of crude NMSBA; conversion of NMSBA to NMSBC; reacting cyclohexanedione with 2-nitro-4-methylsulphonyl benzoyl chloride (NMSBC) to form an enol ester followed by a rearrangement process to give mesotrione; a distillation step; formation of potassium enolate mesotrione solution; one or more purification steps; and crystallisation of mesotrione.

5. A process for preparing mesotrione, said process comprising: oxidation of NMST to give crude NMSBA; optional partial purification of crude NMSBA; conversion of NMSBA to NMSBC; reacting cyclohexanedione with 2-nitro-4-methylsulphonyl benzoyl chloride (NMSBC) to form an enol ester followed by a rearrangement process to give mesotrione; formation of a mesotrione enolate solution; decantation, filtration and adsorption treatment carried out in any order; and crystallisation of mesotrione.

* * * * *